US012793387B2

(12) United States Patent
Gupta et al.

(10) Patent No.: US 12,793,387 B2
(45) Date of Patent: Nov. 10, 2026

(54) URETEROSCOPY IMAGING SYSTEM AND METHODS

(71) Applicants: The Chancellor, Masters and Scholars of the University of Oxford, Oxford (GB); Oxford University Innovation Limited, Oxford (GB); Boston Scientific Scimed Inc., Maple Grove, MN (US)

(72) Inventors: Soumya Gupta, Headington (GB); Sharib Ali, Chapel Allerton (GB); Jens Rittscher, Kidlington (GB); Benjamin Turney, Oxford (GB); Niraj Prasad Rauniyar, Plymouth, MN (US); Aditi Ray, San Jose, CA (US); Longquan Chen, Lexington, MA (US)

(73) Assignees: Boston Scientific Scimed Inc., Maple Grove, MN (US); University of Oxford, Oxford (GB); Oxford University Innovation Limited, Oxford (GB)

( * ) Notice: Subject to any disclaimer, the term of this patent is extended or adjusted under 35 U.S.C. 154(b) by 291 days.

(21) Appl. No.: 18/588,865

(22) Filed: Feb. 27, 2024

(65) Prior Publication Data

US 2024/0296658 A1 Sep. 5, 2024

Related U.S. Application Data

(60) Provisional application No. 63/487,718, filed on Mar. 1, 2023.

(51) Int. Cl.
*G06V 10/764* (2022.01)
*A61B 1/00* (2006.01)
(Continued)

(52) U.S. Cl.
CPC ...... *G06V 10/764* (2022.01); *A61B 1/000095* (2022.02); *A61B 1/000096* (2022.02);
(Continued)

(58) Field of Classification Search
USPC ........................................................ 382/128
See application file for complete search history.

(56) References Cited

U.S. PATENT DOCUMENTS

2023/0050833 A1* 2/2023 Cherubini .............. G06V 10/25
2024/0354949 A1* 10/2024 Sousa Ferreira ...... G06N 3/091

OTHER PUBLICATIONS

Gupta et al: "Multi-class motion-based semantic segmentation for ureteroscopy and laser lithotripsy", Computerized Medical Imaging and Graphics, Pergamon Press, New York, NY, US, vol. 101, Aug. 8, 2022 (Aug. 8, 2022), XP087197933, ISSN: 0895-6111, DOI: 10.1016/J.COMPMEDIMAG.2022.102112 (Year: 2022).*

(Continued)

*Primary Examiner* — Jacky X Zheng
(74) *Attorney, Agent, or Firm* — Seager, Tufte & Wickhem, LLP

(57) ABSTRACT

This disclosure teaches multi-classification of endoscopic imaging using a segmentation neural network. The network is trained on imaging data using a novel loss function with components of both focal and boundary loss. During a lithotripsy procedure, images are received by a deployed endoscopic probe. Based on the received imaging data and inference data from its prior learning, the segmentation neural network identifies renal calculi and surgical instruments within the imaging data. The imaging data is modified and displayed to assist the lithotripsy procedure.

18 Claims, 8 Drawing Sheets

(51) Int. Cl.

| | |
|---|---|
| ***A61B 1/307*** | (2006.01) |
| ***A61B 18/26*** | (2006.01) |
| ***G06V 10/14*** | (2022.01) |
| ***G06V 10/22*** | (2022.01) |
| ***G06V 10/26*** | (2022.01) |
| ***G06V 10/34*** | (2022.01) |
| ***G06V 10/774*** | (2022.01) |
| ***G06V 10/776*** | (2022.01) |
| ***G06V 10/82*** | (2022.01) |

(52) U.S. Cl.
CPC .......... *A61B 1/00045* (2013.01); *A61B 1/307* (2013.01); *A61B 18/26* (2013.01); *G06V 10/14* (2022.01); *G06V 10/22* (2022.01); *G06V 10/26* (2022.01); *G06V 10/34* (2022.01); *G06V 10/774* (2022.01); *G06V 10/776* (2022.01); *G06V 10/82* (2022.01); *G06V 2201/034* (2022.01)

(56) References Cited

OTHER PUBLICATIONS

Gupta et al., "Multi-Class Motion-Based Semantic Segmentation for Ureteroscopy and Laser Lithotripsy," Computerized Medical Imaging and Graphics, Pergamon Press, New York, NY, vol. 101, 14 pages, Aug. 8, 2022.
International Search Report and Written Opinion for International Application No. PCT/US2024/017475, dated Jun. 6, 2024, (12 pages).
Gupta et al., "Multi-class motion-based semantic segmentation for ureteroscopy and laser lithotripsy," Computerized Medical Imaging and Graphics, vol. 101, No. 102112, 14 pages, Available online Aug. 8, 2022.

* cited by examiner

UERETEROSCOPY IMAGING SYSTEM AND METHODS

CROSS-REFERENCE TO RELATED APPLICATIONS

This application claims the benefit of U.S. Provisional Patent Application Ser. No. 63/487,718 filed Mar. 1, 2023, the disclosure of which is incorporated herein by reference.

TECHNICAL FIELD

The present disclosure generally relates to endoscopy imaging procedures. Particularly, but not exclusively, the present disclosure relates to the processing of renal calculi images during endoscopic lithotripsy.

BACKGROUND

One procedure to address renal calculi, also known as kidney stones, is ureteral endoscopy, also known as ureteroscopy. A probe with a camera or other sensor is inserted into the patient's urinary tract to find and destroy the calculi. An ideal procedure is one in which the medical professional quickly identifies and smoothly eliminates each of the kidney stones.

Adequately dealing with a kidney stone requires correctly estimating its size, shape, and composition so that the correct tool or tools can be used to identify and address it. Because an endoscopic probe is used rather than the surgeon's own eyes, it may not always be clear from the returned images exactly where or how big each calculus is. A need therefore exists for an imaging system for ureteral endoscopy that provides the operator with automatically-generated information in tandem with the received images.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

The present disclosure provides ureteral endoscopic imaging solutions that address shortcomings in conventional solutions. For example, the systems according to the present disclosure can provide timely information during the lithotripsy procedure determined by automatically classifying portions of the visual field as renal calculi and as surgical implements.

In general, the present disclosure provides for accurate classification of endoscopic image data based on a segmentation neural network trained by deformation vector data and an improved loss function. When renal calculi and surgical components are correctly distinguished from other items in the visual field, the image displayed to the medical practitioner can be modified to assist in the procedure.

In some examples, the present disclosure provides a method of endoscopic imaging, comprising: receiving, from an endoscopic probe while it is deployed, imaging data of a visual field including one or more renal calculi and one or more surgical instruments; analyzing the received imaging data using a segmentation neural network; generating, from the network analysis, a classification of the visual field into spatial regions, wherein a first spatial region is classified as one or more renal calculi and a second, distinct spatial region is classified as one or more surgical instruments; and based on the classification of the visual field, modifying a display of the imaging data provided during deployment of the endoscopic probe; wherein the segmentation neural network analyzes the imaging data based on machine learning of training data performed using a loss function with both region-based and contour-based loss components.

In some implementations, the segmentation neural network machine learning is performed using a deformation vector field network. In some implementations, the loss function used in the machine learning of the segmentation neural network further includes a cross-correlation loss component from one or more warped images generated by the deformation vector field network. In some implementations, the loss function used in the machine learning of the segmentation neural network further includes a smoothing component from one or more deformation vector field maps generated by the deformation vector field network. In some implementations, the deformation vector field network is an encoding-decoding neural network having both linear and non-linear convolution layers.

In some implementations, the machine learning further includes augmentation performed on the training data. In some implementations, the data augmentation includes two or more of the following applied stochastically to images within the training data: horizonal flip, vertical flip, shift scale rotate, sharpen, Gaussian blur, random brightness contrast, equalize, and contrast limited adaptive histogram equalization (CLAHE). In some implementations, the data augmentation includes random brightness contrast and at least one of equalize and CLAHE applied stochastically to images within the training data.

In some implementations, the one or more surgical instruments comprise a laser fiber. In some implementations, the endoscopic probe is deployed during a lithotripsy procedure. In some implementations, the display of the modified imaging data occurs during the lithotripsy procedure and is provided to a medical practitioner to assist in the ongoing lithotripsy procedure.

The method may further comprise while the endoscopic probe is still deployed, receiving additional imaging data; generating an updated classification of the visual field based on the additional imaging data; and further modifying the display of the imaging data based on the updated classification. In some implementations, modifying the display of the imaging data comprises adding one or more properties of the one or more renal calculi to the display.

In some embodiments, the present disclosure can be implemented as a computer readable storage medium comprising instructions, which when executed by a processor of a computing device cause the processor to implement any of the methods described herein. With some embodiments, the present disclosure can be implemented as a computer comprising a processor; and memory comprising instructions, which when executed by the processor cause the computing system to implement any of the methods described herein.

In some examples, the present disclosure can be implemented as a computing system, comprising: a processor; a display; and memory comprising instructions, which when executed by the processor cause the computing system to: receive, from an endoscopic probe while it is deployed, imaging data of a visual field including one or more renal calculi and one or more surgical instruments; analyze the received imaging data using a segmentation neural network; generate, from the network analysis, a classification of the visual field into spatial regions, wherein a first spatial region is classified as one or more renal calculi and a second, distinct spatial region is classified as one or more surgical instruments; and based on the classification of the visual field, modify a display of the imaging data provided on the display during deployment of the endoscopic probe; wherein the segmentation neural network analyzes the imaging data based on machine learning of training data performed using a loss function with both region-based and contour-based loss components.

In some implementations, the segmentation neural network machine learning is performed using a deformation vector field network.

In some implementations, the loss function used in the machine learning of the segmentation neural network further includes a cross-correlation loss component from one or more warped images generated by the deformation vector field network. In some implementations, the loss function used in the machine learning of the segmentation neural network further includes a smoothing component from one or more deformation vector field maps generated by the deformation vector field network. In some implementations, the deformation vector field network is an encoding-decoding neural network having both linear and non-linear convolution layers.

In some examples, the disclosure includes a computer readable storage medium comprising instructions, which when executed by a processor of a computing device causes the processor to receive, from an endoscopic probe while it is deployed, imaging data of a visual field including one or more renal calculi and one or more surgical instruments; analyze the received imaging data using a segmentation neural network; generate, from the network analysis, a classification of the visual field into spatial regions, wherein a first spatial region is classified as one or more renal calculi and a second, distinct spatial region is classified as one or more surgical instruments; and based on the classification of the visual field, modify a display of the imaging data provided during deployment of the endoscopic probe; wherein the segmentation neural network analyzes the imaging data based on machine learning of training data performed using a loss function with both region-based and contour-based loss components. In some embodiments, the segmentation neural network machine learning is performed using a deformation vector field network

BRIEF DESCRIPTION OF THE SEVERAL VIEWS OF THE DRAWINGS

To easily identify the discussion of any element or act, the most significant digit or digits in a reference number refer to the figure number in which that element is first introduced.

DETAILED DESCRIPTION

The foregoing has broadly outlined the features and technical advantages of the present disclosure such that the following detailed description of the disclosure may be better understood. It is to be appreciated by those skilled in the art that the embodiments disclosed may be readily utilized as a basis for modifying or designing other structures for carrying out the same purposes of the present disclosure. The novel features of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Some of the devices and methods explained in the present disclosure are also described in S. Gupta et al., "Multi-class motion-based semantic segmentation for ureteroscopy and laser lithotripsy," *Computerized Medical Image and Graphics* (2022), which is hereby incorporated by reference in its entirety as though explicitly included herein.

Figure 1:
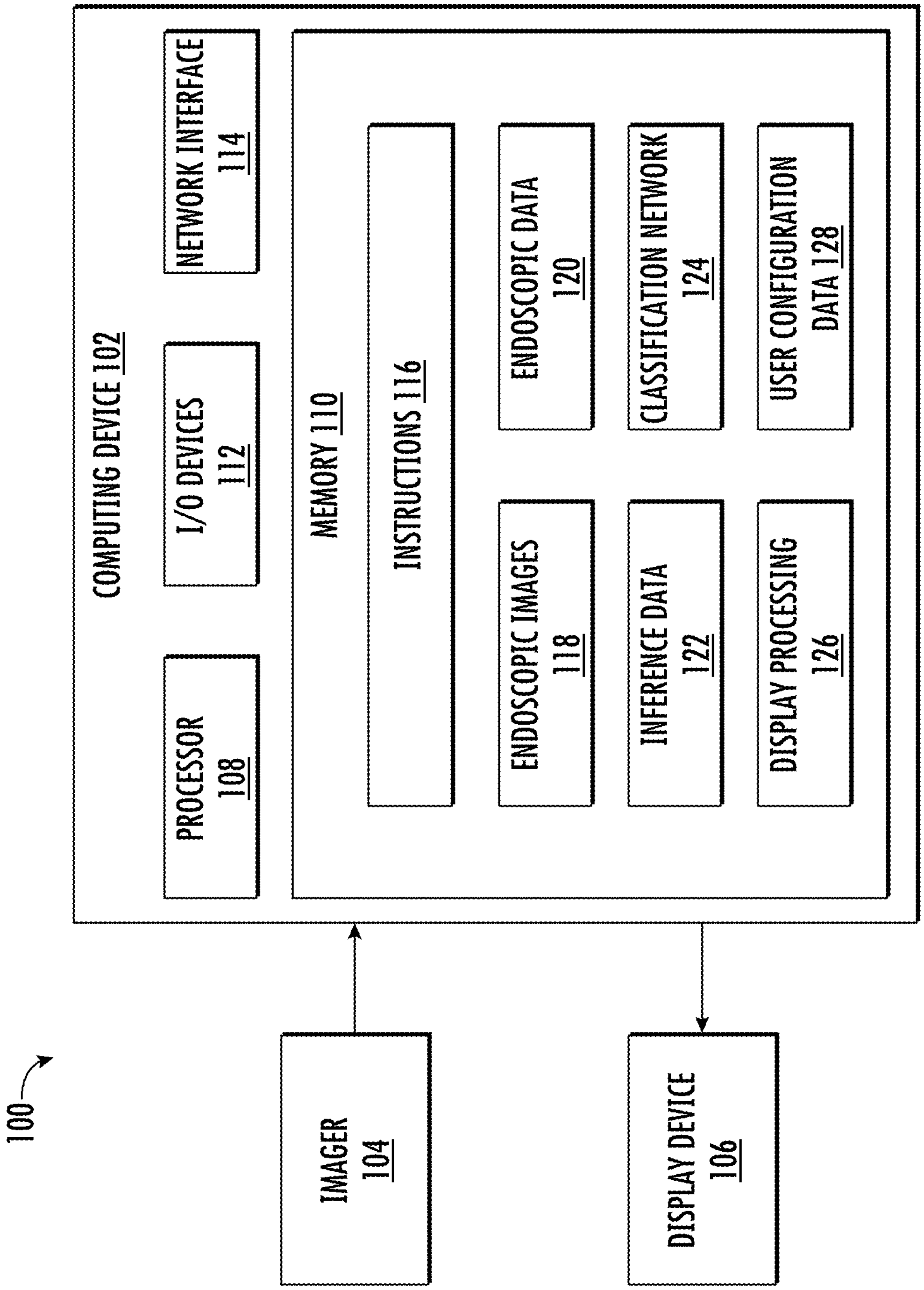
FIG. 1 illustrates an endoscopic imaging system, in accordance with embodiment(s) of the present disclosure.

FIG. 1 illustrates an endoscopic imaging system 100, in accordance with non-limiting examples of the present disclosure. In general, an endoscopic imaging system 100 is a system for processing and displaying images in real-time that are captured by an endoscope deployed for lithotripsy. Although the present disclosure focuses of lithotripsy, which would use a ureteroscope, the disclosure is applicable to other urological or endoscopic modalities and/or applications, such as, for example, utilizing duodenoscopes, gastroscopes, colonoscopes, bronchoscopes, etc.

Endoscopic imaging system 100 includes a computing device 102. Optionally, endoscopic imaging system 100 includes imager 104 and display device 106. In an example, computing device 102 can receive an image or a group of images representing a patient's urinary tract. For example, computing device 102 can receive endoscopic images 118 from imager 104. In some embodiments, imager 104 can be a camera or other sensor deployed with an endoscope during a lithotripsy procedure.

Although the disclosure uses visual-spectrum camera images to describe illustrative embodiments, imager 104 can be any endoscopic imaging device, such as, for example, a fluoroscopy imaging device, an ultrasound imaging device, an infrared or ultraviolet imaging device, a computed tomography (CT) imaging device, a magnetic resonance (MR) imaging device, a positron emission tomography (PET) imaging device, or a single-photon emission computed tomography (SPECT) imaging device.

Imager 104 can generate information elements, or data, including indications of renal calculi. Computing device 102 is communicatively coupled to imager 104 and can receive the data including the endoscopic images 118 from imager 104. In general, endoscopic images 118 can include indications of shape data and/or appearance data of the urinary tract. Shape data can include landmarks, surfaces, and boundaries of the three-dimensional surfaces of the urinary tract. With some examples, endoscopic images 118 can be constructed from two-dimensional (2D) or three-dimensional (3D) images.

In general, display device 106 can be a digital display arranged to receive rendered image data and display the data in a graphical user interface. Computing device 102 can be any of a variety of computing devices. In some embodiments, computing device 102 can be incorporated into and/or implemented by a console of display device 106. With some embodiments, computing device 102 can be a workstation or server communicatively coupled to imager 104 and/or display device 106. With still other embodiments, computing device 102 can be provided by a cloud-based computing device, such as, by a computing as a service system accessibly over a network (e.g., the Internet, an intranet, a wide area network, or the like). Computing device 102 can include processor 108, memory 110, input and/or output (I/O) devices 112, and network interface 114.

The processor 108 may include circuitry or processor logic, such as, for example, any of a variety of commercial processors. In some examples, processor 108 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 108 may include graphics processing portions and may include dedicated memory, multiple-threaded processing and/or some other parallel processing capability. In some examples, the processor 108 may be an application specific integrated circuit (ASIC) or a field programmable integrated circuit (FPGA).

The memory 110 may include logic, a portion of which includes arrays of integrated circuits, forming non-volatile memory to persistently store data or a combination of non-volatile memory and volatile memory. It is to be appreciated, that the memory 110 may be based on any of a variety of technologies. In particular, the arrays of integrated circuits included in memory 110 may be arranged to form one or more types of memory, such as, for example, dynamic random access memory (DRAM), NAND memory, NOR memory, or the like.

I/O devices 112 can be any of a variety of devices to receive input and/or provide output. For example, I/O devices 112 can include, a keyboard, a mouse, a joystick, a foot pedal, a display (e.g., touch, non-touch, or the like) different from display device 106, a haptic feedback device, an LED, or the like. One or more features of the endoscope may also provide input to the imaging system 100.

Network interface 114 can include logic and/or features to support a communication interface. For example, network interface 114 may include one or more interfaces that operate according to various communication protocols or standards to communicate over direct or network communication links. Direct communications may occur via use of communication protocols or standards described in one or more industry standards (including progenies and variants). For example, network interface 114 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like. Additionally, network interface 114 can include logic and/or features to enable communication over a variety of wired or wireless network standards (e.g., 802.11 communication standards). For example, network interface 114 may be arranged to support wired communication protocols or standards, such as, Ethernet, or the like. As another example, network interface 114 may be arranged to support wireless communication protocols or standards, such as, for example, Wi-Fi, Bluetooth, ZigBee, LTE, 5G, or the like.

Memory 110 can include instructions 116 and endoscopic images 118. During operation, processor 108 can execute instructions 116 to cause computing device 102 to receive endoscopic images 118 from imager 104 via input and/or output (I/O) devices 112. Processor 108 can further execute instructions 116 to identify urinary structures and material in need of removal. Further still, processor 108 can execute instructions 116 to generate images to be displayed on display device 106. Memory 110 can further include endoscope data 120 that provides information about endoscope systems, including visible endoscope components.

Memory 110 can further include inference data 122 generated from machine learning processes described further herein. The inference data 122 may include, for example, the weights given to each node used in a classification network 124 as described.

The classification network 124 is a neural network used to classify portions of the visual field represented by the endoscopic images into one of multiple different objects. The classification network 124 may, for example, classify a first set of target objects (renal calculi) and a second set of surgical tools (laser fibers) from the rest of the visual field.

Memory 110 can further include a display processing module 126, including the tools necessary to augment endoscopic images with the calculated values, and user configuration data 128 to reference when customizable options are made available to a user.

The classification network 124 is a multi-layer neural network that uses inference data provided by machine learning on training data prior to the use of the endoscope in surgery. The framework for one such machine learning process is illustrated in FIG. 2.

Generating Inference Data

Figure 2:
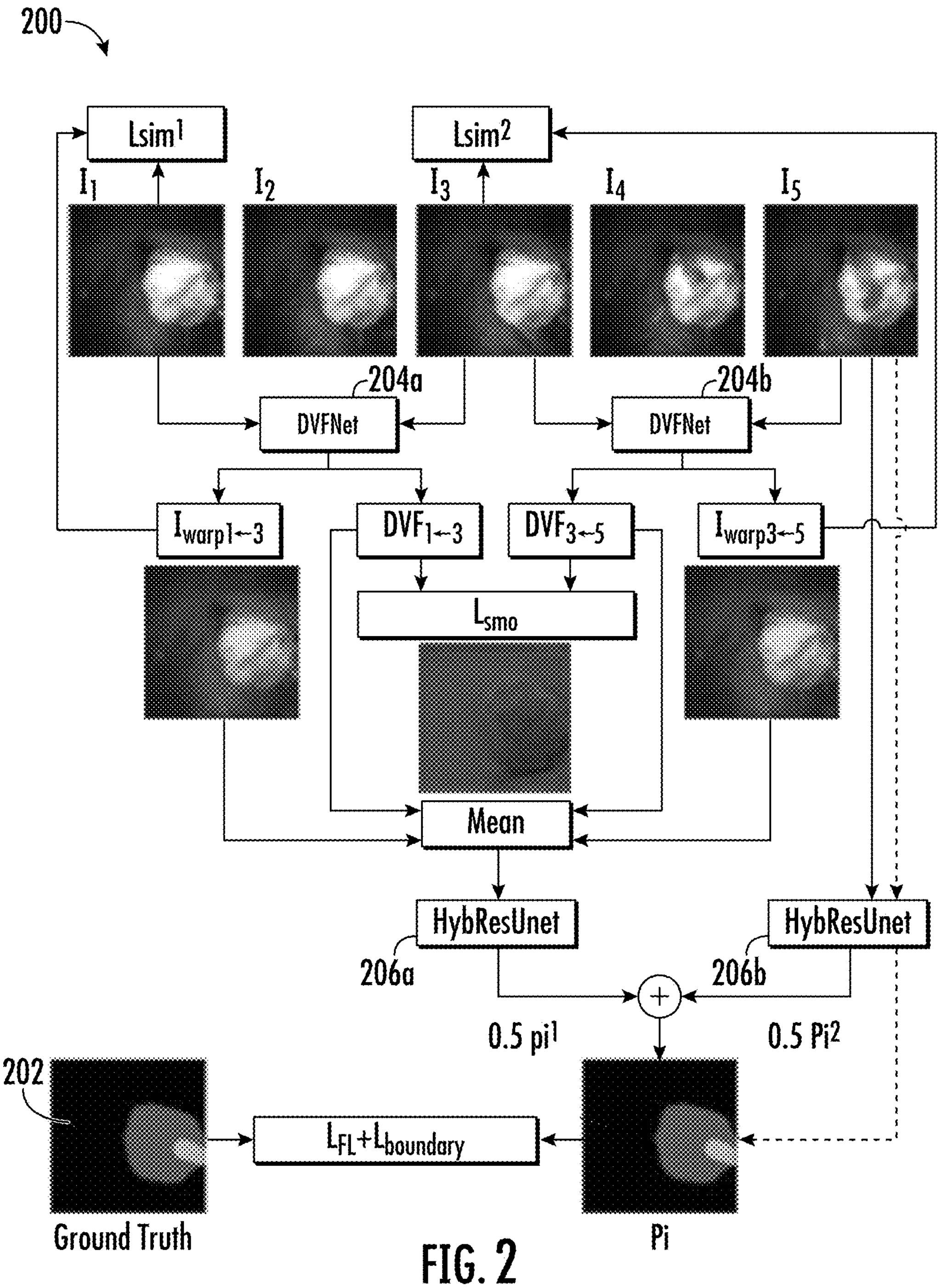
FIG. 2 illustrates a framework for training a segmentation neural network to generate inference data, in accordance with embodiment(s) of the present disclosure.

In FIG. 2, a machine learning framework 200 to generate inference data is shown. The framework 200 processes a clip sequence $I_1$-$I_5$ against ground truth data 202 provided for the field of view covered by the sequence. Image pairs ($I_1$, $I_3$) and ($I_3$, $I_5$) are each fed into an encoder-decoder network architecture 204*a* and 204*b*, each of which generates a deformation vector field map ($DVF_{1\leftarrow 3}$ and $DVF_{3\leftarrow 5}$) and a warped image ($I_{warp1\leftarrow 3}$ and $I_{warp3\leftarrow 5}$).

Figure 3:
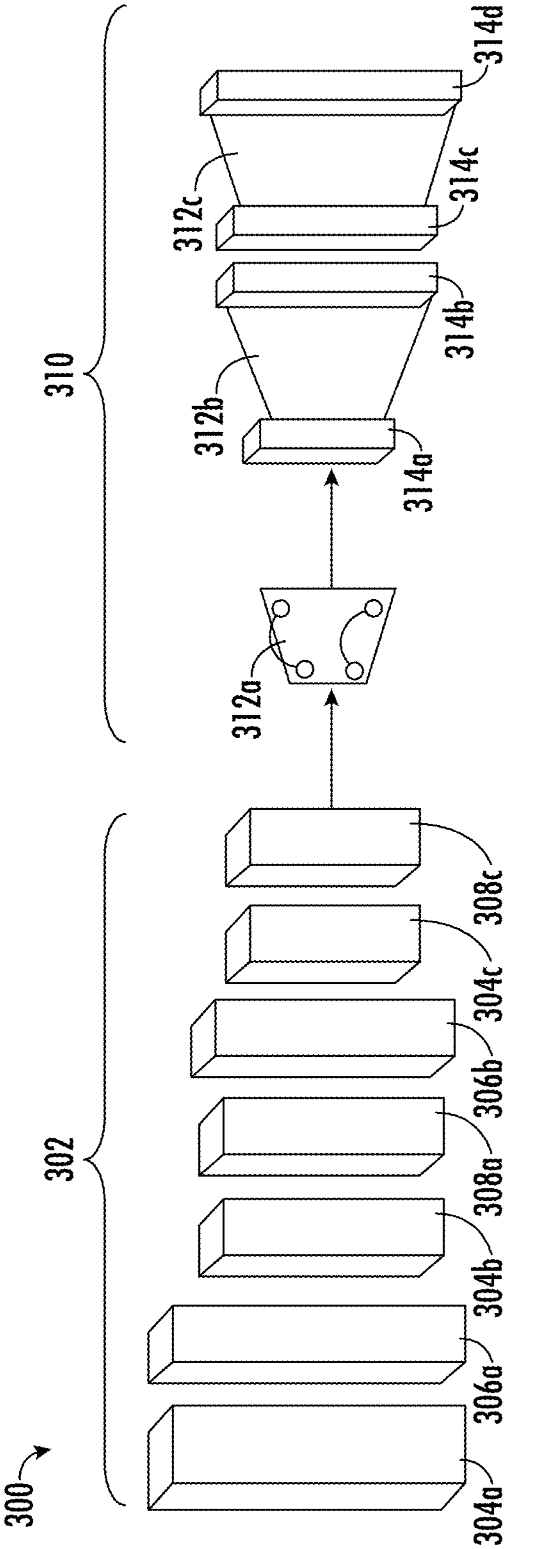
FIG. 3 illustrates a deformation vector field neural network in accordance with embodiments(s) of the present disclosure.

FIG. 3 shows an encoder-decoder network architecture as used in 204*a* and 204*b*. The image registration neural network 300 uses motion between adjacent frames to compute end-to-end deformation vector fields. As shown, the network 300 has an encoder 302 with three linear convolutional layers 304*a-c*, two average pooling layers 306*a* and 306*b*, and two deformable convolutional layers 308*a* and 308*b*, although other numbers and configurations of layers may be used in other implementations.

Each of the five convolutional layers 304*a-c*, 306*a*, and 306*b* may, in some implementations, include batch normalization and exponential layer unit processing. In other implementations, one or both of these processing techniques may only be used selectively or stochastically within some but not all of the convolutional layers.

The product of the encoder 306 is then fed into the decoder 310, which in turn consists of three spline resamplers 312*a-c* interleaved with convolutional layers 314*a-d*. In some implementations, the convolutional layers 314*a-d* associated with the decoder 310 may include an exponential layer unit processing, but not batch normalization processing.

Each of the three spline resamplers 312*a-c* have parameters that are optimized within the machine learning data. In some implementations, the spline resamplers 312*a-c* may each be a Catmull-Rom spline resampler with the same parameters, as determined from the use of training data that forms the objective of machine learning within the registration network 300.

The parameters used for the spline resampler within each registration neural network may, in some implementations, be identical between the first network architecture 204*a* and the second network architecture 204*b*. Furthermore, the parameters used in the spline resampler may vary based on other known aspects of the situation, such as the location of the endoscope or the stage of the procedure. In some implementations, training data produced during in vitro use of the endoscope (images taken in a closed container under controlled conditions) may require different parameters and processing than training data produced during in vivo use (images taken during live endoscopic surgery).

Registration network architecture 204*a* produces two data results: a distortion vector field map $DVF_{1\leftarrow 3}$ and a warped image $I_{warp1\leftarrow 3}$, while registration network architecture 204*b* produces a second distortion vector field map $DVF_{3\leftarrow 5}$ and second warped image $I_{warp3\leftarrow 5}$. Each of these results is then candidate data for the classification network 206*a*.

In some implementations, the data result used to train the classification network 206*a* may depend on based on the circumstances of the image data, such as whether the data was produced in vitro or in vivo. In some implementations, data produced in vitro may result in the mean of the distortion vector field maps $DVF_{1\leftarrow 3}$ and $DVF_{3\leftarrow 5}$ being used as the input for the classification network 206*a*, while in vivo data may result in the warped images $I_{warp1\leftarrow 3}$ and $I_{warp3\leftarrow 5}$ being used.

Figure 4:
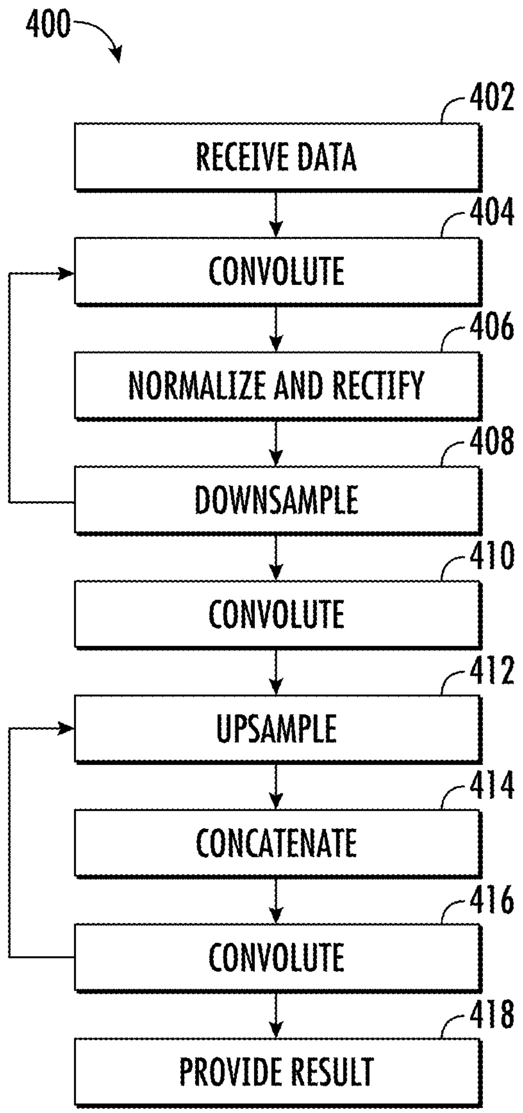
FIG. 4 illustrates a logic flow for a segmentation neural network in accordance with embodiments(s) of the present disclosure.

FIG. 4 illustrates the logic flow 400 associated with a classification network that is trained based on the data processed as described above. The classification network is a semantic segmentation encoder-decoder network using residual blocks.

At block 402, the network receives the image data, which may be a warped image or distortion vector field map depending on exterior circumstances. As further described below with respect to both training data and eventual use of the inference data, the image data may also be a data frame.

Blocks 404, 406, and 408 represent an encoder path in which the data is contracted (downsampled) multiple times. In one implementation, the system performs these steps including downsampling a total of four times during implementation of the classification network, although it will be understood that more or fewer times are possible depending on the available computational resources and the size of the original endoscopic images.

At block 404, two sequential 3×3 convolutions are used on the data. At block 406, the data is subject to batch normalization and rectified linear unit (ReLU) processing, using the pre-convoluted data in conjunction with the convoluted result. At block 408, the data is downsampled. In some implementations, a 2×2 max pooling operations with a stride of 2 is used. The result is then used as the input for the next round of convolution for the length of the encoder path.

Once the number of cycles representing the coder path have completed, at block 410 the system undergoes convolution again. This may be the same residual block convolution as at block 404, including two sequential 3×3 convolutions.

Blocks 412, 414, and 416 comprise a decoder path in which the data is expanded (upsampled) as many times as the data was contracted during the encoder path. At block 412, the data is upsampled by using transposed and regular convolutions to increase the image size. At block 414, the upsampled data is concatenated with the processed image of the same size from immediately before downsampling. At block 416, additional sequential convolutions are again used, as they were at block 404.

At block 418, after each of the encoder and decoder paths have resolved, the semantic segmentation network returns an image.

Two of the classification networks, as described in logic flow 400, are used during the machine learning process for determining the inference data: a first classification network 206*a*, which receives data from the DVF networks, and a second classification network 206*b*, which processes a frame I5 without distortion vector field processing. In some implementations, the DVF network process uses only greyscale images while the frame I5 taken and processed directly by the classification network 206*b* may be a full color image. The results $p_i^1$ and $p_i^2$ returned by the classification networks are then averaged and compared to the ground truth image 202 to generate elements of the loss function that is minimized.

Loss Function

The training data, as described above, is used to minimize a compound loss function as follows:

$$L = L_{FL} + \alpha L_{boundary} + \beta L_{sim} + \zeta L_{smo}$$

The hyper-parameters α, β, and ζ can be used to adjust the contribution of the different components to the loss function. $L_{FL}$ is focal loss, defined as $$L_{FL} = -(1-\hat{p}_y)^{\gamma}\log(\hat{p}_y)$$

where y is an integer from 0 to C−1 for C different classes, $\hat{p}$ is a probability vector with C dimensions representing the estimated probability distribution over the C different classes having $\hat{p}_y$ as its value for class γ, and γ is a tunable non-negative scaling factor.

The boundary loss, $L_{boundary}$, is defined as $$L_{boundary} = 1 - B^c = 1 - (2\,P^c\,R^c)/(P^c + R^c)$$

where the boundary metric Bc is measured in terms of the precision Pc and recall Rc, averaged over all of the C classes. The precision and recall are, in turn, calculated as $$P^c = \frac{\mathrm{sum}(y^b_{pd} \circ y^{b,ext}_{gt})}{\mathrm{sum}(y^b_{pd})} \quad R^c = \frac{\mathrm{sum}(y^b_{gt} \circ y^{b,ext}_{pd})}{\mathrm{sum}(y^b_{gt})}$$

where ○ is pixel-wise multiplication and sum( ) is pixel-wise summation. $y^b_{gt}$ and $y^b_{pd}$ are boundary regions defined based on the binary maps $y_{gt}$ and $y_{pd}$ for ground truth and network prediction, respectively, and are in turn defined as:

$$y^b_{gt} = \text{pool}(1 - y_{gt}, \theta_\circ) - (1 - y_{gt}) \quad y^b_{pd} = \text{pool}(1 - y_{pd}, \theta_\circ) - (1 - y_{pd})$$

where pool( ) is a pixel-wise max-pooling operation with $\theta_\circ$ is the sliding window size. The extended boundaries can then be given as $$y^{b,ext}_{gt} = \text{pool}(y^b_{gt}\theta) \quad y^{b,ext}_{pd} = \text{pool}(y^b_{pd}\theta)$$

with a window θ that may be larger than $\theta_\circ$.

As noted from the illustration of FIG. 2, above, the focal and boundary losses $L_{FT}$ and $L_{boundary}$ are each calculated by comparing image data fully processed by the classification network to training data. Two other loss calculations are also included in the loss that is optimized during this learning procedure, and these components $L_{sim}$ and $L_{smo}$ are calculated from results of the deformation vector field networks.

Cross-correlation loss between the warped images $I_{warp1\leftarrow3}$ and $I_{warp3\leftarrow5}$ with their corresponding source image $I_1$ and $I_3$ is given by:

$$L_{sim} = \frac{1}{2N}\sum\left(\frac{I_1(x) - \mu_1}{\sqrt{\sigma_1^2 + \varepsilon^2}} - \frac{I_{wrap_{1\leftarrow3}}(x) - \mu_{wrap_{1\leftarrow3}}}{\sqrt{\sigma^2_{wrap_{1\leftarrow3}} + \varepsilon^2}}\right)^2 + \frac{1}{2N}\sum\left(\frac{I_3(x) - \mu_2}{\sqrt{\sigma_2^2 + \varepsilon^2}} - \frac{I_{wrap_{3\leftarrow5}}(x) - \mu_{wrap_{3\leftarrow5}}}{\sqrt{\sigma^2_{wrap_{3\leftarrow5}} + \varepsilon^2}}\right)^2$$

where μ and σ are the mean and standard deviation, N is the total number of pixels, and ε is a small positive value to avoid division by zero, such as 0.001.

Local smoothness loss on the estimated deformation vector field gradients is given by:

$$L_{smo} = \sum\left(\|\nabla DVF_{1\leftarrow3}\|_2^2 + \|\nabla DVF_{3\leftarrow5}\|_2^2\right)$$

representing the sum of the L2 norms of the flow gradients of the vector fields.

The parameters of the classification network are varied in order to minimize the loss equation L with these four sub-components, and this produces the inference values that are used to classify images during the endoscopic procedure.

Live Endoscopic Image Processing

Figure 5:
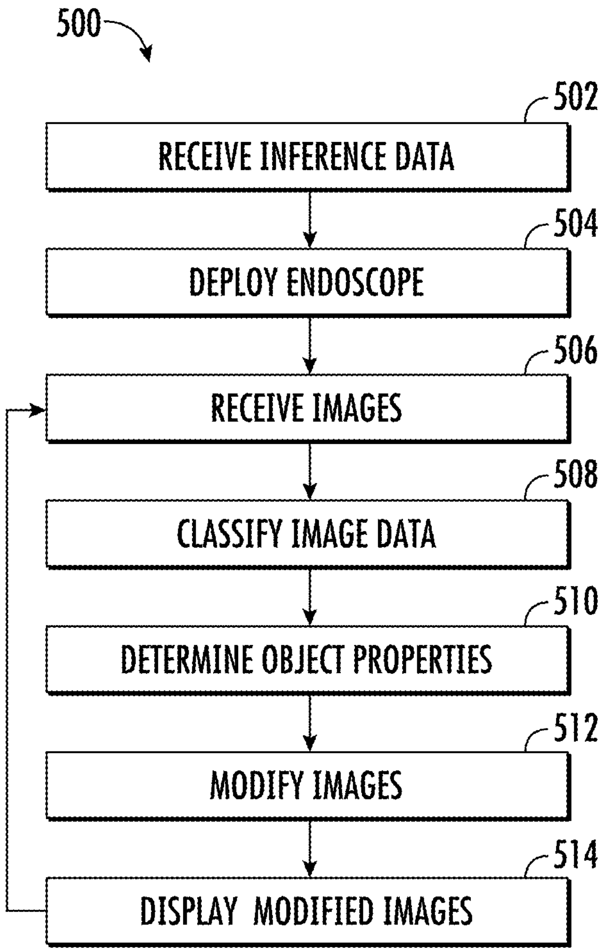
FIG. 5 illustrates a logic flow for endoscopic image processing in accordance with embodiments(s) of the present disclosure.

FIG. 5 shows logic 500 for processing and displaying images during endoscopic lithotripsy. Although logic flow 500 is described with reference to endoscopic imaging system 100 and FIG. 1, examples are not limited by this and logic flow 500 could be implemented by a system having components not depicted in FIG. 1.

At block 502, the system 100 receives inference data, which may have been stored in system memory 110 when the inference data was generated if it was generated locally or may be accessed from another system. In some implementations, the inference data may be preloaded with the classification network; that is, when the system 100 is first configured with the classification neural network used to classify images, the parameters used as inference data may already be provided for use during the procedure.

At block 504, the endoscope is deployed as part of a lithotripsy procedure. Techniques of lithotripsy vary based on the needs of the patient and the available technology. Any part of the urinary tract may be the destination of the endoscope, and the procedure may target renal calculi in different locations during a single procedure.

The remainder of the logic flow 500, representing blocks 506-514, takes place while the endoscope is deployed and the lithotripsy procedure is carried out. These steps 506-514 represent an image being captured, processed, and displayed to the medical professional performing the procedure. The displayed images are "live," meaning the delay between receiving and displaying the images is short enough that the images can be used by the professional to control the lithotripsy tools in real time based on what is displayed.

At block 506, the system receives one or more endoscopic images from the imager. The system may process more than one image at once, based on expected processing latency as well as the imager's rate of capturing images; each individual image is referred to as a "frame" and the speed of capture as the "framerate". For example, where the system might take as much as 0.1 seconds to process a set of frames and the imager has a framerate of 50 frames per second, the system might process 5 or more frames as a set to have sufficient throughput to process the available data. The system may also process fewer than all the received frames; in some implementations it may select a fraction of the received frames such as every second or third frame to process.

Figure 6A:
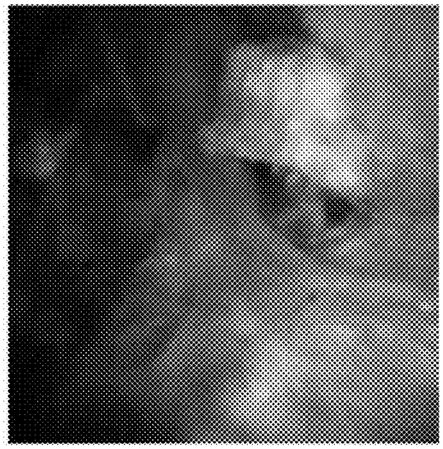
FIG. 6A is an endoscopic image, in accordance with embodiment(s) of the present disclosure.

FIG. 5A illustrates an endoscopic image 500, representing a single "frame" captured by an imager during deployment of an endoscope for lithotripsy. Although shown in greyscale for FIG. 6A, the system receives and processes a color image (which may, for example, represent a standard RGB or CMYK encoding, or any other image format that can be read and displayed). Two renal calculi and a laser fiber are visible in the image.

Figure 6B:
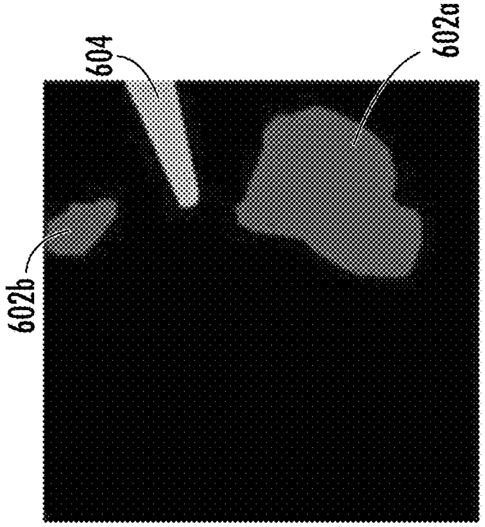
FIG. 6B is a classification result from the use of a segmentation neural network on FIG. 6A, in accordance with embodiment(s) of the present disclosure.

At block 508, the system classifies the received image data into target objects (renal calculi) and surgical tools (laser fiber) by use of the classification neural network 124 as described. FIG. 6B shows the result of the processing of FIG. 6A (which may again, although shown in greyscale, be processed in color by the neural network). Two regions 602*a* and 602*b* are classified as target objects, while one region 604 is classified as a surgical tool.

At block 510, the system determines properties of the identified objects. This may include establishing the depth from the endoscopic probe of the renal calculi and/or the surgical tools, estimating the size of any of the identified objects, determining the temperature or materials of the objects, or any other automated process engaged by the system based on the classification. In some implementations, further image processing algorithms, simulation models, or even neural networks may be used to determine the properties of the classified objects.

Figure 6C:
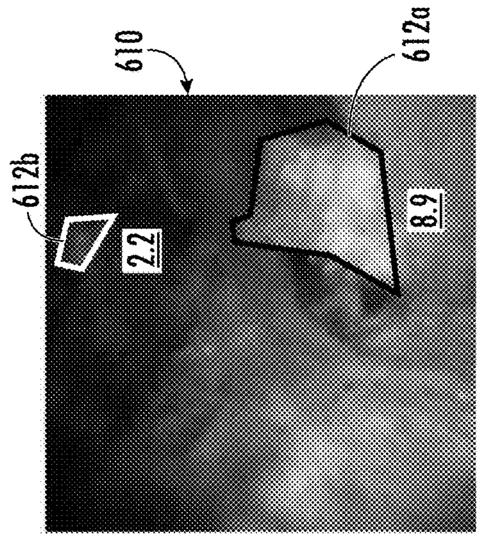
FIG. 6C is a display of a modified endoscopic image in accordance with embodiment(s) of the present disclosure.

At block 512, the images are modified based on the classification and the identified properties, and then at block 514, the modified images are displayed. FIG. 6C illustrates an example of a display image 610 with added markings 612*a* and 612*b* showing the size of the renal calculi. A rough polygonal outline of each image is displayed along with a label denoting the size of the object in millimeters. For the larger renal calculus, the markings 612*a* are in black, while the markings 612*b* for the smaller renal calculus are in white. The color of the markings may represent some aspect of the object, such as its size relative to a threshold, but may also be selected either automatically or manually based on other factors of the display such as contrast for legibility.

The system may include a timer before the displayed values are changed. For example, even if the system processes a new set of frames 10 times per second, once a value has been determined and output for display, it may be 1 second before that display value can be changed. This is to avoid the display fluctuating so rapidly as to reduce its value to the users.

Figure 7:
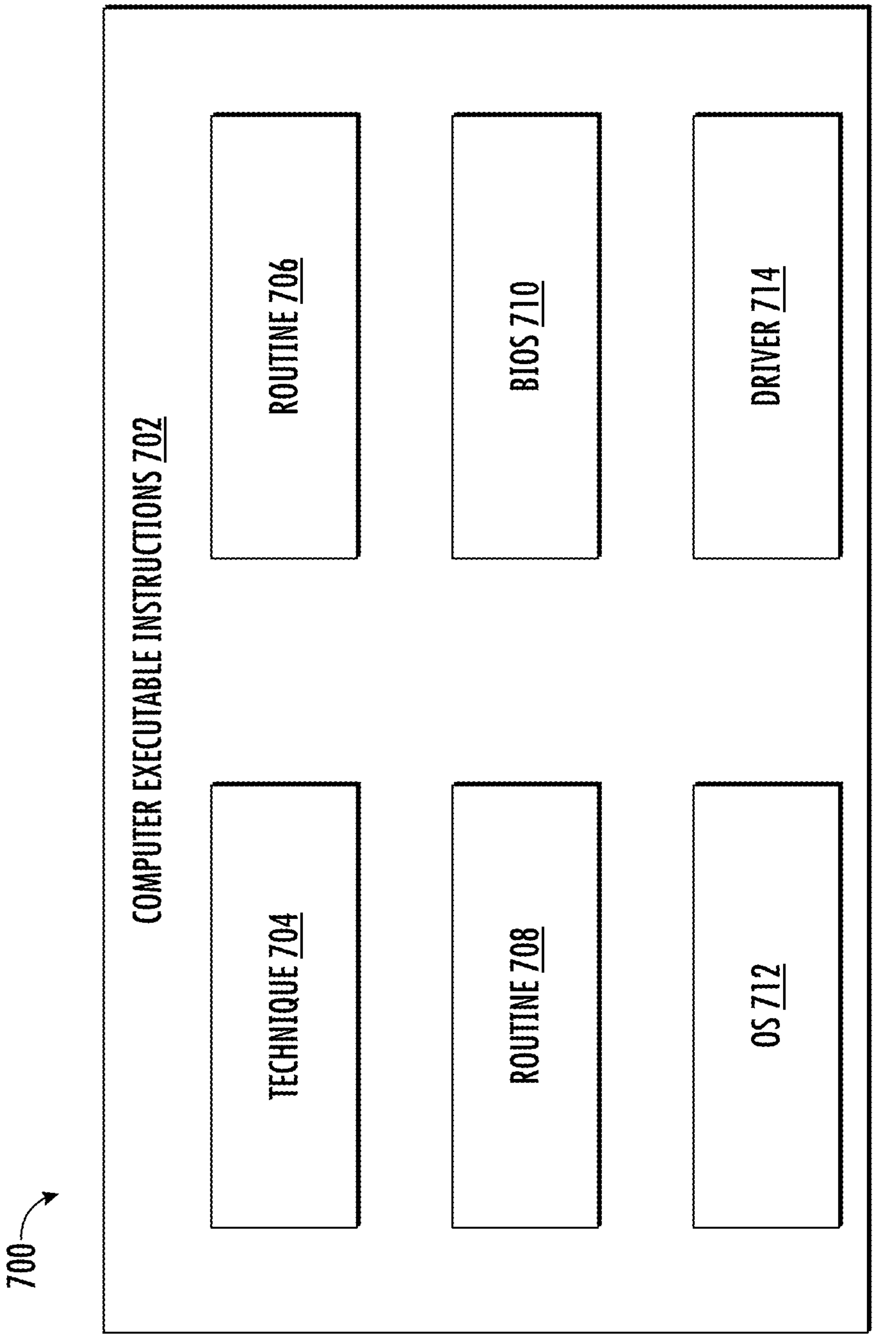
FIG. 7 illustrates a computer-readable storage medium 700 in accordance with one embodiment.

FIG. 7 illustrates computer-readable storage medium 700. Computer-readable storage medium 700 may comprise any non-transitory computer-readable storage medium or machine-readable storage medium, such as an optical, magnetic or semiconductor storage medium. In various embodiments, computer-readable storage medium 700 may comprise an article of manufacture. In some embodiments, the medium 700 may store computer executable instructions 702 with which circuitry (e.g., processor(s) or the like) can execute. For example, computer executable instructions 702 can include instructions to implement operations described with respect to technique 704, routine 706, routine 708, BIOS 710, OS 712, and/or driver 714. Examples of computer-readable storage medium 700 or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions 702 may include any suitable type of code, such as source code, compiled code, interpreted code, executable code, static code, dynamic code, object-oriented code, visual code, and the like.

Figure 8:
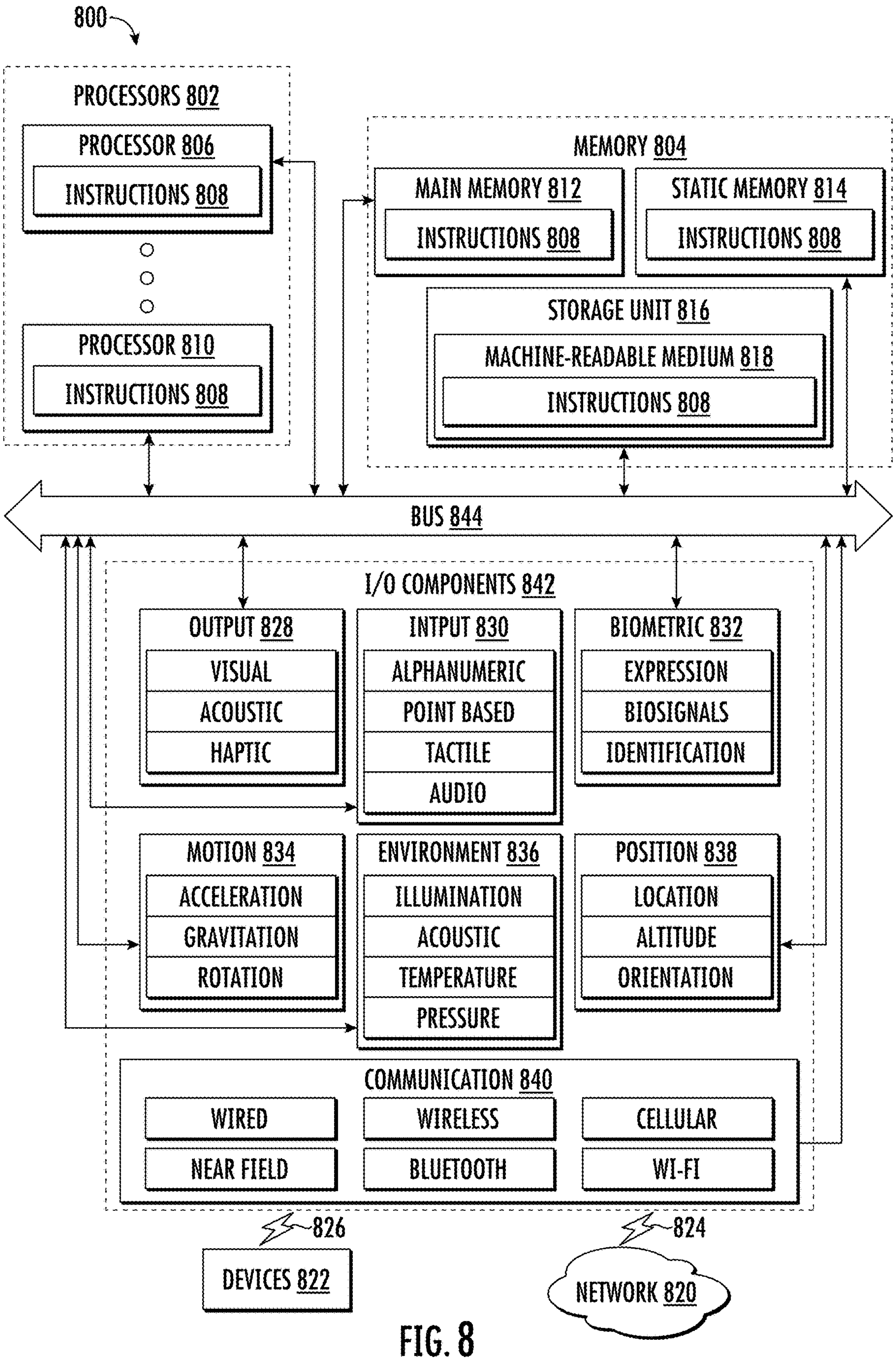
FIG. 8 illustrates a diagrammatic representation of a machine 800 in the form of a computer system within which a set of instructions may be executed for causing the machine to perform any one or more of the methodologies discussed herein, according to an example embodiment.

FIG. 8 illustrates a diagrammatic representation of a machine 800 in the form of a computer system within which a set of instructions may be executed for causing the machine to perform any one or more of the methodologies discussed herein. More specifically, FIG. 8 shows a diagrammatic representation of the machine 800 in the example form of a computer system, within which instructions 808 (e.g., software, a program, an application, an applet, an app, or other executable code) for causing the machine 800 to perform any one or more of the methodologies discussed herein may be executed. For example the instructions 808 may cause the machine 800 to execute technique 704 of FIG. 7, routine 706 of FIG. 7, routine 708 of FIG. 7, or the like. More generally, the instructions 808 may cause the machine 800 to allocate memory during pre-boot operations and preserve the memory for post-boot operations (or usage).

The instructions 808 transform the general, non-programmed machine 800 into a particular machine 800 programmed to carry out the described and illustrated functions in a specific manner. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 808, sequentially or otherwise, that specify actions to be taken by the machine 800. Further, while only a single machine 800 is illustrated, the term "machine" shall also be taken to include a collection of machines 800 that individually or jointly execute the instructions 808 to perform any one or more of the methodologies discussed herein.

The machine 800 may include processors 802, memory 804, and I/O components 842, which may be configured to communicate with each other such as via a bus 844. In an example embodiment, the processors 802 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 806 and a processor 810 that may execute the instructions 808. The term "processor" is intended to include multi-core processors that may comprise two or more independent processors (sometimes referred to as "cores") that may execute instructions contemporaneously. Although FIG. 8 shows multiple processors 802, the machine 800 may include a single processor with a single core, a single processor with multiple cores (e.g., a multi-core processor), multiple processors with a single core, multiple processors with multiples cores, or any combination thereof.

The memory 804 may include a main memory 812, a static memory 814, and a storage unit 816, both accessible to the processors 802 such as via the bus 844. The main memory 804, the static memory 814, and storage unit 816 store the instructions 808 embodying any one or more of the methodologies or functions described herein. The instructions 808 may also reside, completely or partially, within the main memory 812, within the static memory 814, within machine-readable medium 818 within the storage unit 816, within at least one of the processors 802 (e.g., within the processor's cache memory), or any suitable combination thereof, during execution thereof by the machine 800.

The I/O components 842 may include a wide variety of components to receive input, provide output, produce output, transmit information, exchange information, capture measurements, and so on. The specific I/O components 842 that are included in a particular machine will depend on the type of machine. For example, portable machines such as mobile phones will likely include a touch input device or other such input mechanisms, while a headless server machine will likely not include such a touch input device. It will be appreciated that the I/O components 842 may include many other components that are not shown in FIG. 8. The I/O components 842 are grouped according to functionality merely for simplifying the following discussion and the grouping is in no way limiting. In various example embodiments, the I/O components 842 may include output components 828 and input components 830. The output components 828 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 830 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 842 may include biometric components 832, motion components 834, environmental components 836, or position components 838, among a wide array of other components. For example, the biometric components 832 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 842 may include communication components 840 operable to couple the machine 800 to a network 820 or devices 822 via a coupling 824 and a coupling 826, respectively. For example, the communication components 840 may include a network interface component or another suitable device to interface with the network 820. In further examples, the communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 822 may be another machine or any of a wide variety of peripheral devices (e.g., a peripheral device coupled via a USB).

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geolocation, location via Wi-Fi® signal triangulation, location via detecting an NFC beacon signal that may indicate a particular location, and so forth.

The various memories (i.e., memory 804, main memory 812, static memory 814, and/or memory of the processors 802) and/or storage unit 816 may store one or more sets of instructions and data structures (e.g., software) embodying or utilized by any one or more of the methodologies or functions described herein. These instructions (e.g., the instructions 808), when executed by processors 802, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 820 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 820 or a portion of the network 820 may include a wireless or cellular network, and the coupling 824 may be a Code Division Multiple Access (CDMA) connection, a Global System for Mobile communications (GSM) connection, or another type of cellular or wireless coupling. In this example, the coupling 824 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 808 may be transmitted or received over the network 820 using a transmission medium via a network interface device (e.g., a network interface component included in the communication components 840) and utilizing any one of a number of well-known transfer protocols (e.g., hypertext transfer protocol (HTTP)). Similarly, the instructions 808 may be transmitted or received using a transmission medium via the coupling 826 (e.g., a peer-to-peer coupling) to the devices 822. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 808 for execution by the machine 800, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

What is claimed is:

1. A method of endoscopic imaging, comprising:

receiving, from an endoscopic probe while it is deployed, imaging data of a visual field including one or more renal calculi and one or more surgical instruments;

analyzing the received imaging data using a segmentation neural network;

generating, from the network analysis, a classification of the visual field into spatial regions, wherein a first spatial region is classified as one or more renal calculi and a second, distinct spatial region is classified as one or more surgical instruments; and based on the classification of the visual field, modifying a display of the imaging data provided during deployment of the endoscopic probe;

wherein the segmentation neural network analyzes the imaging data based on machine learning of training data performed using a loss function with both region-based, cross-correlation derived from deformation vector field-based warped images, and contour-based loss components.

2. The method of claim 1, wherein the segmentation neural network machine learning is performed using a deformation vector field network.

3. The method of claim 2, wherein the loss function used in the machine learning of the segmentation neural network further includes a smoothing component from one or more deformation vector field maps generated by the deformation vector field network.

4. The method of claim 2, wherein the deformation vector field network is an encoding-decoding neural network having both linear and non-linear convolution layers.

5. The method of claim 1, wherein the machine learning further includes augmentation performed on the training data.

6. The method of claim 5, wherein the data augmentation includes two or more of the following applied stochastically to images within the training data: horizonal flip, vertical flip, shift scale rotate, sharpen, Gaussian blur, random brightness contrast, equalize, and contrast limited adaptive histogram equalization (CLAHE).

7. The method of claim 6, wherein the data augmentation includes random brightness contrast and at least one of equalize and CLAHE applied stochastically to images within the training data.

8. The method of claim 1, wherein the one or more surgical instruments comprise a laser fiber.

9. The method of claim 1, wherein the endoscopic probe is deployed during a lithotripsy procedure.

10. The method of claim 9, wherein the display of the modified imaging data occurs during the lithotripsy procedure and is provided to a medical practitioner to assist in the ongoing lithotripsy procedure.

11. The method of claim 1, further comprising:

while the endoscopic probe is still deployed, receiving additional imaging data;

generating an updated classification of the visual field based on the additional imaging data; and further modifying the display of the imaging data based on the updated classification.

12. The method of claim 1, wherein modifying the display of the imaging data comprises adding one or more properties of the one or more renal calculi to the display.

13. A computing system, comprising:

a processor;

a display; and memory comprising instructions, which when executed by the processor cause the computing system to:

receive, from an endoscopic probe while it is deployed, imaging data of a visual field including one or more renal calculi and one or more surgical instruments;

analyze the received imaging data using a segmentation neural network;

generate, from the network analysis, a classification of the visual field into spatial regions, wherein a first spatial region is classified as one or more renal calculi and a second, distinct spatial region is classified as one or more surgical instruments; and based on the classification of the visual field, modify a display of the imaging data provided on the display during deployment of the endoscopic probe;

wherein the segmentation neural network analyzes the imaging data based on machine learning of training data performed using a loss function with both region-based, cross-correlation derived from deformation vector field-based warped images, and contour-based loss components.

14. The computing system of claim 13, wherein the segmentation neural network machine learning is performed using a deformation vector field network.

15. The computing system of claim 13, wherein the loss function used in the machine learning of the segmentation neural network further includes a smoothing component from one or more deformation vector field maps generated by the deformation vector field network.

16. The computing system of claim 13, wherein the deformation vector field network is an encoding-decoding neural network having both linear and non-linear convolution layers.

17. A non-transitory computer readable storage medium comprising instructions, which when executed by a processor of a computing device cause the processor to:

receive, from an endoscopic probe while it is deployed, imaging data of a visual field including one or more renal calculi and one or more surgical instruments;

analyze the received imaging data using a segmentation neural network;

generate, from the network analysis, a classification of the visual field into spatial regions, wherein a first spatial region is classified as one or more renal calculi and a second, distinct spatial region is classified as one or more surgical instruments; and based on the classification of the visual field, modify a display of the imaging data provided during deployment of the endoscopic probe;

wherein the segmentation neural network analyzes the imaging data based on machine learning of training data performed using a loss function with both region-based, cross-correlation derived from deformation vector field-based warped images, and contour-based loss components.

18. The computer readable storage medium of claim 17, wherein the segmentation neural network machine learning is performed using a deformation vector field network.

* * * * *